United States Patent [19]

Hrvojic

[11] Patent Number: 4,538,452
[45] Date of Patent: Sep. 3, 1985

[54] BORE-HOLE HYDRAULICS SIMULATOR

[75] Inventor: Ivan Hrvojic, Mississauga, Canada

[73] Assignee: Ontario Research Foundation, Sheridan Park, Canada

[21] Appl. No.: 551,343

[22] Filed: Nov. 14, 1983

[51] Int. Cl.³ ............................................. G01N 15/04
[52] U.S. Cl. .................................. 73/61.4; 73/432 SD
[58] Field of Search ................ 73/61.4, 61 R, 432 SD

[56] References Cited

U.S. PATENT DOCUMENTS

| | | | |
|---|---|---|---|
| 2,733,595 | 2/1956 | Twining | 73/61.4 X |
| 3,172,286 | 3/1965 | Grubb et al. | 73/61.4 |
| 3,872,710 | 3/1975 | Louvel | 73/61.4 X |
| 4,020,676 | 5/1977 | Nuxhall et al. | 73/61 R |
| 4,397,177 | 8/1983 | Cain | 73/61.4 |
| 4,446,726 | 5/1984 | Hockenberry | 73/61.4 |

Primary Examiner—Stewart J. Levy
Assistant Examiner—Joseph W. Roskos
Attorney, Agent, or Firm—Sim & McBurney

[57] ABSTRACT

A bore hold hydraulics simulator for drilling fluid is disclosed, in which the drilling fluid is flowed along a permeable partition which divides a first volume containing the drilling fluid from a second volume adapted to collect filtrate passing through the permeable partition. A pressure differential is established across the partition so as to promote the passage of filtrate into the second volume, and a vessel is provided for collecting the filtrate passing into the second volume.

30 Claims, 3 Drawing Figures

BORE-HOLE HYDRAULICS SIMULATOR

This invention relates generally to a method and apparatus for measuring the filter cake qualities of a drilling fluid for use in well-drilling, and has particular relevance to dynamic conditions for drilling fluids, capable of accounting for the filtration characteristics under conditions approximating those encountered under actual operating conditions.

BACKGROUND OF THIS INVENTION

As is well known, drilling fluid is utilized in well-drilling operations for a number of basic purposes. One purpose is to cool and lubricate the bit and the string. Another is to carry up to the surface the chips of rock, etc. which are produced as a result of the drilling operation. A third purpose is to deposit a tough, impermeable filter cake against the sides of the bore-hole and thus block up the tiny interstices in the rock wall through which the fluid phase of the drilling fluid could escape. A fourth is to control the pressure in the well in order to prevent "blow-out" due to a higher pressure in the formation than in the well. A fifth is for control of corrosion of the string and bit. A sixth purpose is to stabilize the well bore chemistry. A seventh is to buoyantly support the drill string.

Due to geothermal heat in the surrounding formations, the temperature of the drilling fluids can rise as high as 600° F. or more. The pressure of the drilling fluid depends, of course, upon the depth of the bore-hole. For very deep wells, the pressure placed upon the drilling fluid at the bottom of the well can be as high as 20,000 psi or more.

It is very important for the drilling fluid not only to "cake" and seal against the sides of the bore-hole at locations where the liquid portion of the drilling fluid tends to filter away into the surrounding rock formation, but also to provide a cake layer which will resist erosion by the flowing of the drilling fluid upwardly in contact with the bore-hole walls, and will lessen friction between the drill string and the bore-hole walls.

The pertinent prior art contains patents which are adapted to test the caking quality of a drilling fluid, but none of these is capable of doing so under conditions in which the fluid itself flows past an element simulating permeability and pore size of a rock formation. Moreover, the prior art methods and apparatuses do not have the capability of carrying out this testing under conditions of high pressure and temperature such as those found under actual drilling conditions.

U.S. Pat. No. 2,217,175, Ledbetter, issued Oct. 8, 1940, relates to a method and apparatus for testing drilling fluids, in which the caking quality of the fluid has an effect upon the length of time taken for the fluid phase of the slurry, after contact with a filter paper, to percolate radially outwardly along the filter paper.

U.S. Pat. No. 2,646,678, Standing, issued July 28, 1953, relates to a device adapted to determine filter loss in drilling fluids under static conditions, and is not capable of taking into account the erosion rate resulting from drilling fluid flowing past a caked layer on the sides of a bore-hole.

U.S. Pat. No. 2,830,266, Southwick, issued Apr. 8, 1958, is of general interest in that it discloses a method and apparatus for filtering drilling fluid within a bore-hole, by obtaining a specimen of the filter cake and then measuring the thickness and/or the electrical properties of the filter cake.

U.S. Pat. No. 3,055,208, Gallus, issued Sept. 25, 1962, discloses a filter adapted to measure the rate and extent to which fluids are lost to sub-surface strata from drilling fluids, under conditions up to 1,000 psi.

U.S. Pat. No. 3,172,286, Grubb, issued Mar. 9, 1965, also discloses apparatus intended to test certain characteristics of drilling fluids.

GENERAL DESCRIPTION OF THIS INVENTION

It is the object of an aspect of this invention to provide a compact, high-strength, reliable apparatus adapted to test the filter cake qualities resulting from a simulated bore hole environment analogous to those encountered in an actual drilling procedure, including high temperature and high pressure, which incorporates structure that allows the drilling fluid to flow past an element simulating permeability and pore size of a rock formation, through which element a fluid phase of the drilling fluid seeps.

An object of another aspect of this invention is to provide a method for carrying out the dynamic filtration testing of a drilling fluid, taking into account the erosion characteristics of the cake.

Accordingly, this invention provides a bore hole hydraulics simulator for drilling fluid, which includes means for flowing the drilling fluid along a permeable partition which divides a first volume containing the drilling fluid from a second volume adapted to collect filtrate passing through the permeable partition, and means for placing a pressure differential across the permeable partition so as to promote the passage of filtrate into the second volume. Further means are provided for collecting the filtrate passing into the second volume.

This invention further provides a method for testing filtration rate for a drilling fluid filter cake under dynamic and static conditions, comprising several steps. Firstly, the drilling fluid is flowed along a permeable partition which divides a first volume containing the drilling fluid from a second volume adapted to collect filtrate passing through the permeable partition. A pressure differential is placed across the permeable partition so as to promote the passage of filtrate into the second volume, and filtrate passing into the second volume is collected.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 1:
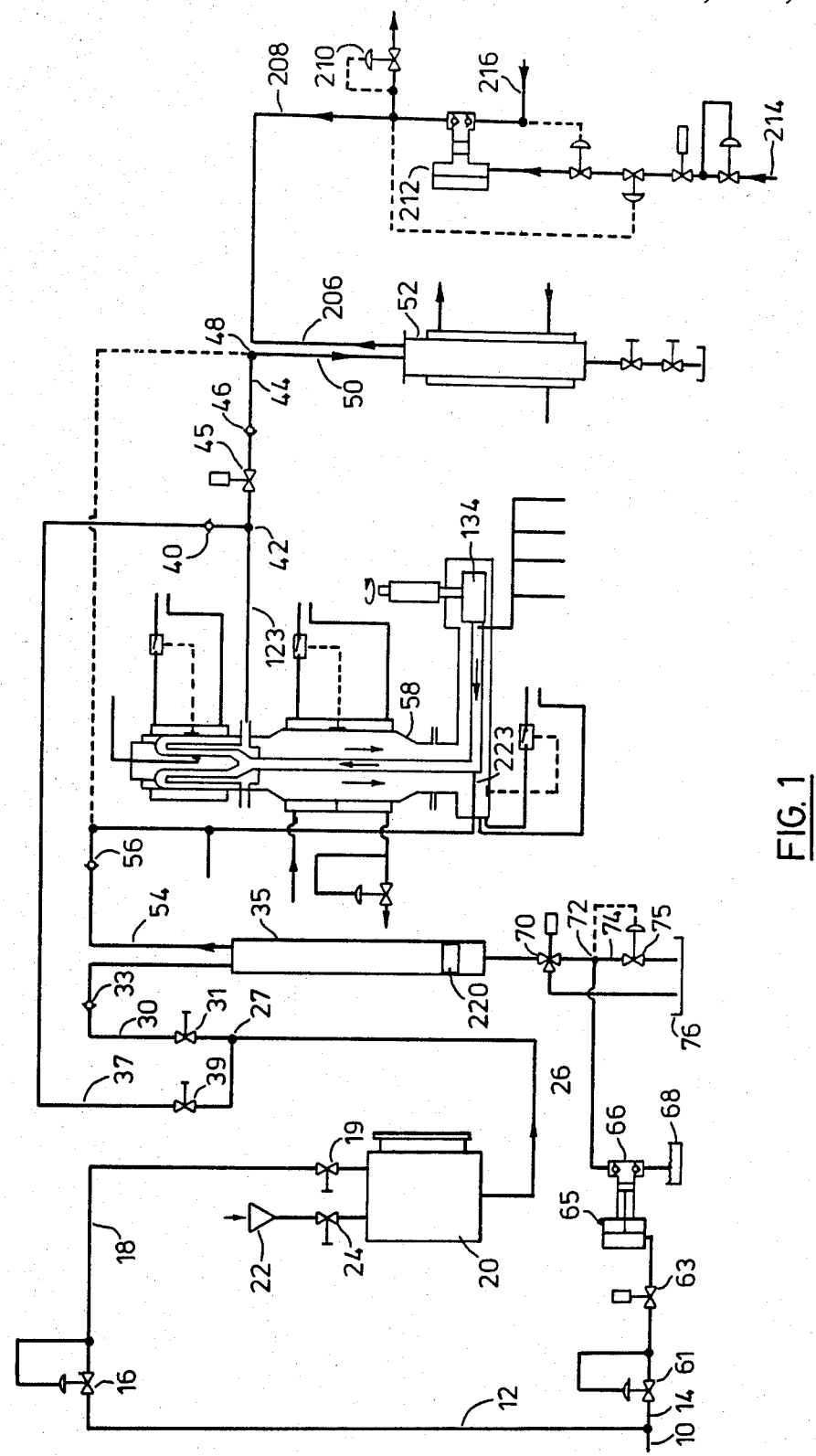
FIG. 1 is a diagrammatic view of the various components of an apparatus constructed in accordance with this invention.

To the left in FIG. 1, a line 10 carries air at 100 psi. The line 10 branches into a line 12 and a line 14. The line 12 leads to an air pressure regulator 16, which is connected by a line 18 with a valve 19, the latter being connected into a filling vessel 20. A hopper 22 allows mud to pass through a valve 24 and into the filling vessel 20.

From the bottom of the filling vessel 20, a mud line 26 passes to a branching point 27 from which a first line 30 containing a shut-off valve 31 and a check valve 33 passes to the top of a fluid compression vessel 35. A second mud line 37 from the branching point 27 contains a shut-off valve 39 and a check valve 40, and this leads to a junction point 42 connecting with a line 44 having a shut-off valve 45 and a check valve 46. From a further junction point 48, a line 50 connects with the top of a filtrate vessel 52.

From the top of the fluid compression vessel 35, a mud outlet line 54 containing a check valve 56 passes to the bottom of the fluid testing vessel 58. The details of the construction of the fluid testing vessel 58 will be described subsequently with respect to FIG. 2.

The line 14, connected at left with the initial pressurized air line 10, contains a pressure regulator 61, and a solenoid valve 63. Air from this line is admitted to the large end of a step-up double piston apparatus 65, which operates a liquid pump 66 that draws liquid from a storage vessel 68 and supplies it through a solenoid valve 70 to the lower end of the fluid compression vessel 35. Extending from a junction point 72 is a drain line 74 having a valve 75 and emptying into a reservoir 76.

Figure 2:
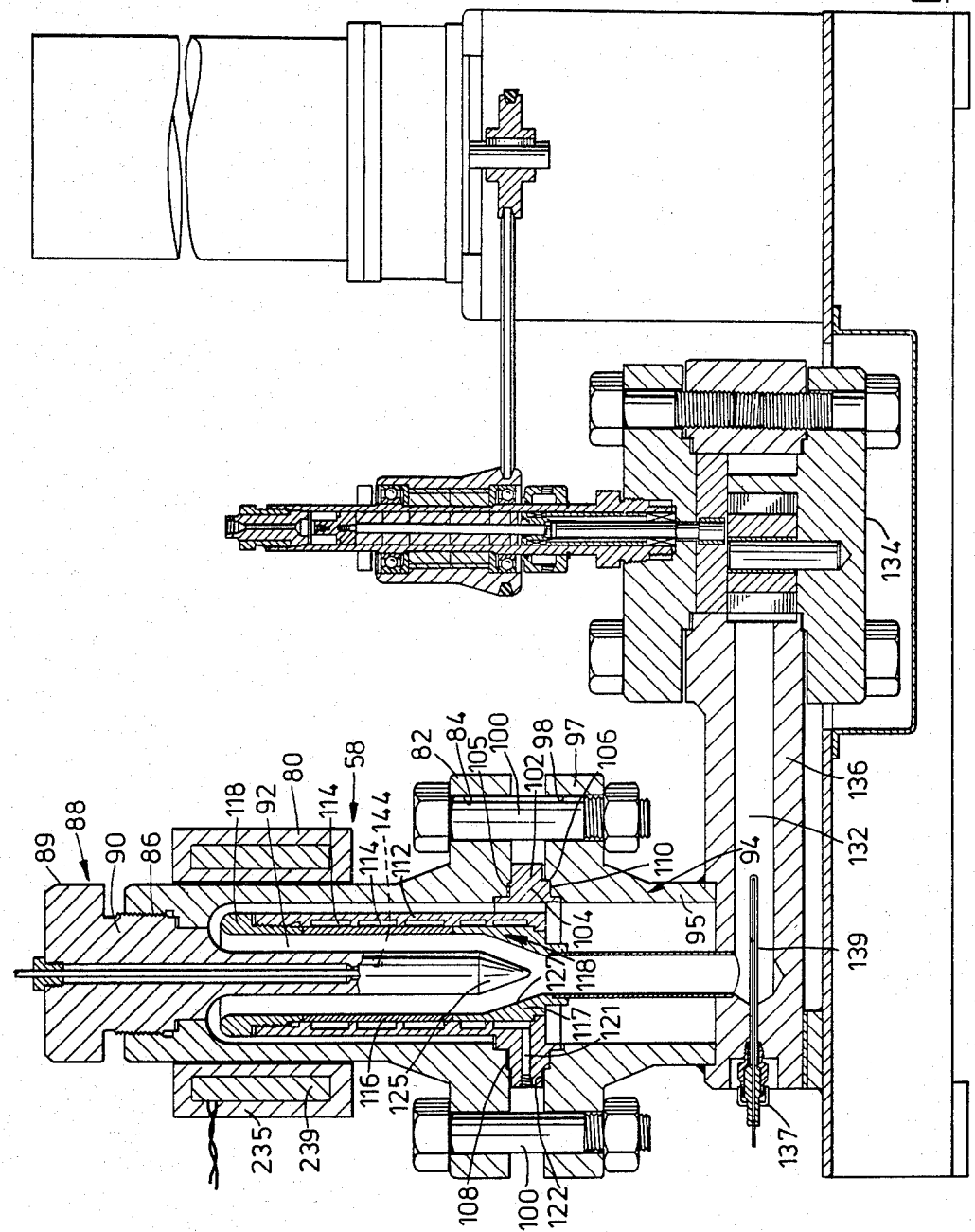
FIG. 2 is a sectional view through the main filtration unit including its circulating pump means.

Attention is now directed to FIG. 2, which shows the fluid testing vessel 58 to include a main cylindrical body 80 having a flange 82 for clamping purposes, the flange 82 being provided with a plurality of circumferentially separated bolt holes 84. At the top, the cylindrical member 80 has a threaded bore 86 adapted to receive a plug 88 having a hexagonal top portion 89, a screw-threaded portion 90, and a rod-like portion 92, the purpose of which will be explained subsequently. The fluid testing vessel 58 also includes a base member 94 having a downwardly projecting cylindrical portion 95 and a flange 97, the flange having bolt holes 98 corresponding to the bolt holes 84 in the flange 82, such that when the bolt holes are in alignment, a plurality of bolts 100 can be placed therethrough in order to tighten the flanges together. The flanges sandwich between them an insert member 102 having a stepped portion 104 for cooperation with stepped portions 105 and 106 of the cylindrical member 80 and the base member 94, respectively. As can be seen in the figure, annular washers 108 and 110 are provided as seals between the various members. The insert 102 includes an upstanding cylindrical portion 112 which comprises inwardly extending ridges 114 adapted to support from the outside a porous, cylindrical partition member 116 which is sandwiched between an upper plug 118 which has a threaded engagement with the top part of the cylindrical portion 112, and a further insert 117 which has a stepped engagement at 118 with the insert 102. Gaskets are provided at the top and bottom of the cylindrical member 116, these being adapted to cushion the cylindrical member 116 against excessive loading. It is contemplated that the porous cylindrical member 116 be constituted of sintered metal, porous ceramic material, or the like, and it is known that certain of these materials can be very brittle. The cylindrical member 116 could also be machined from a sample of the actual rock being drilled, depending upon the strength of the rock.

The space between the porous cylindrical member 116 and the cylindrical portion 112 of the insert 102 exists by virtue of the spacing provided by the ridges 114. The ridges 114 are not continuous, and therefore the entire volume between the cylindrical member 116 and the cylindrical portion 112 can be considered a single volume. This volume is in communication with an outlet duct 121, which has a pipe-threaded female connecting portion 122, to which a suitable conduit, shown in FIG. 2 diagrammatically as the line 123, can be connected. The rod-like member 92 extends centrally downwardly within the plug 118, the porous cylindrical member 116, and the upper part of the further insert 117. Furthermore, the rod-like member 92 has a conically tapered lower end 125, in order to facilitate passage of drilling mud around and along the rod-like member 92. Moreover, the further insert 117 has an internal frusto-conical wall 127, again for promoting smooth flow of the drilling mud.

Below the further insert 117, and within the base member 94, a pipe 130 is provided, the pipe 130 connecting with the passage that surrounds the rod-like member 92, and at its lower end connecting with a delivery passageway 132 from a positive displacement pump 134 of known construction. The annular space around the pipe 130 and within the base member 94 constitutes part of a suction passageway for drilling mud, which leads (by a passageway which is not cut by the section shown in FIG. 2) to the suction side of the positive displacement pump 134. The passageway 132 is defined in a horizontally elongated member 136, into which a mounting means 137 projects a temperature probe 139. The annular passageway between the pipe 130 and the base member 94 connects with a further annular passageway 141 exterior of the cylindrical portion 112 but within the cylindrical member 80, this annular passageway communicating with the top of the passageway between the rod-like member 92 and the porous cylindrical member 116.

It is not necessary to describe the positive displacement pump 134 or its drive in great detail, as this does not constitute the focus of the present invention.

Mounted within the rod-like member 92 is an ultrasonic device 144, which includes an ultrasound generator and an ultrasound receiver, capable of determining the mud cake thickness on the inside wall of the porous cylindrical member 116, during operation.

The ultrasonic device is capable of generating an ultrasound signal in the direction radially outwardly from the rod-like member 92, and this signal then is reflected back by caked mud on the porous cylindrical member 116. The length of time taken for the echo to be picked up by the receiver can be used to determine the thickness of the mud cake.

Figure 3:
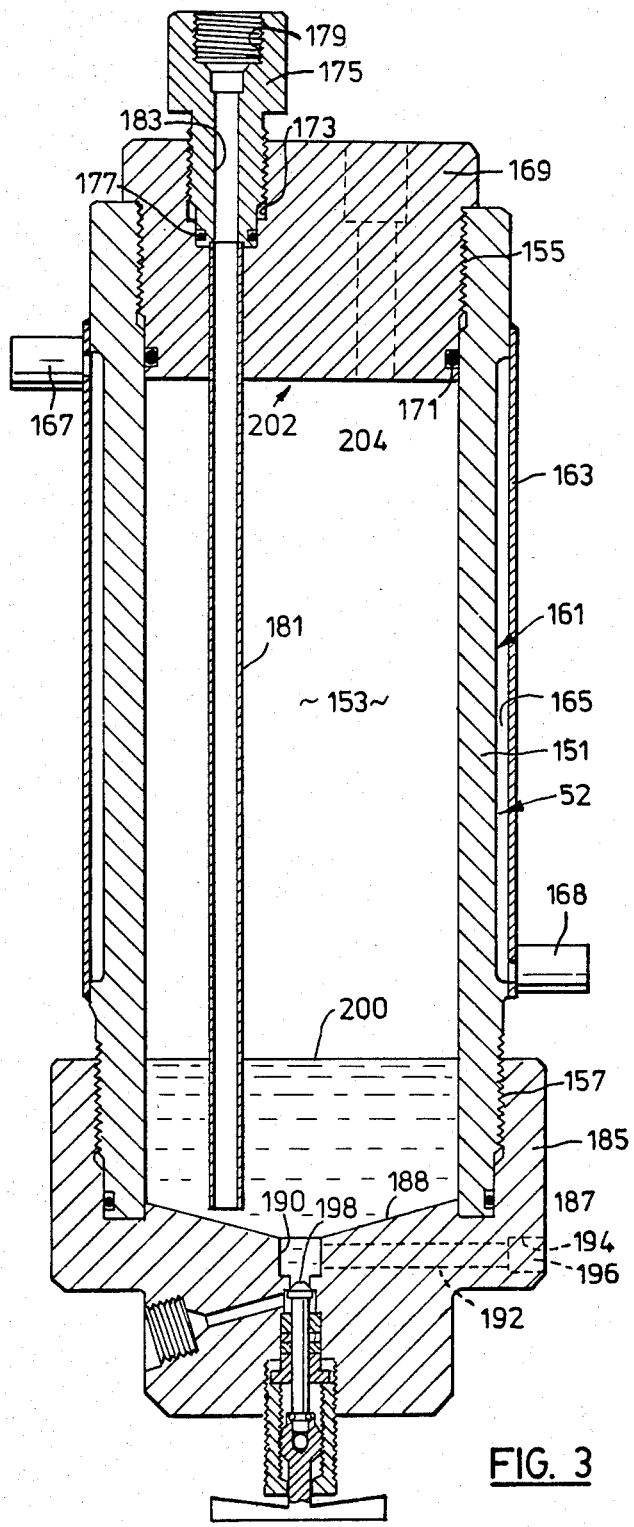
FIG. 3 is an axial sectional view through a filtrate collecting vessel.

Attention is now directed to FIG. 3, which shows the filtrate vessel 52 to a larger scale.

As can be seen, the filtrate vessel consists of a cylindrical member 151 having a hollow cylindrical internal volume 153, internal threads 155 at the upper end, and external threads 157 at the lower end. Intermediately located on the outside wall of the cylindrical member 151 is a recess 161, which is covered by a cylindrical wall 163, the latter being welded at the top and bottom to the cylindrical member 151. The cylindrical wall 161 is spaced from the cylindrical member 151, thus defining an annular space 165 between them. The space 165 is used for cooling purposes, and to this end an inlet connection 167 and an outlet connection 168 are provided at the upper and lower ends, respectively, and antipodally arranged.

A plug member 169 is threaded into the threads 155 at the upper end of the cylindrical member 161, and is provided with an O-ring seal 171 for sealing purposes. Threaded into a threaded bore 173 in the plug member 169 is an inlet connector 175, provided with an O-ring seal 177, and internal threads 179 for receiving a suitable further connector. A tube 181 extends downwardly from the plug member 169 and is in communication with an internal bore 183 of the connector 175, the tube 181 projecting down to a region close to the bottom of the internal volume 153 within the cylindrical member 151.

At the bottom of the cylindrical member 151, the same is threaded into an internal bore defined at the top of a base member 185, the cylindrical member 151 being provided with an O-ring 187 for sealing purposes. The base member 185 defines a downwardly and inwardly converging wall 188 which facilitates drainage of the contents into a central opening 190, the latter being in contact with the end of a transducer rod 192 at the rightward end of which is an ultrasonic means 196 which includes a generator and receiver, and which has the purpose of calibrating a further ultrasonic sensor 198 intended for level measurement within the internal volume 153 of the cylindrical member 151.

The ultrasonic sensor 198 includes ultrasound generating and ultrasound receiving means, and is directed in such a way that the ultrasound travels vertically upwardly so that it will reflect off the surface of filtrate located within the internal volume 153, identified by the numeral 200 in FIG. 3.

It will be understood that the ultrasonic means 196 will be adapted to project an ultrasound signal across the opening 190 which constitutes a cavity of known dimension, and to receive the echo back from the opposite side. Since the cavity defined by the opening 190 has known dimensions, the length of time for the ultrasound to traverse the cavity twice through filtrate located in the cavity will give a value which can be used to calibrate the ultrasonic sensor 198. It will be appreciated that the filtrate entering the internal volume 153 of the filtrate vessel 52 will have different densities at different times, and will change in terms of the speed at which ultrasound is conducted through it. By regularly monitoring the filtrate in the opening 190 using the ultrasonic means 196, the ultrasonic sensor 198 can be regularly adjusted and recalibrated to improve its accuracy.

Another way to determine the amount of filtrate within the internal volume 153 is to project an ultrasound signal from the top central region 202 of the internal volume 153, bounce the same off the surface 200, and then receive the echo again at the top. If one knows the gas pressure above the surface 200 and the constitution of the gas (in this case compressed nitrogen), one will know very accurately the speed of ultrasound travelling through the gas, and therefore the distance from the sensor at the top to the surface 200 can be accurately determined.

The filtrate vessel 52 also has a further opening 204 intended to receive a high pressure gas fitting and to allow gas above the level of the filtrate to be exhausted out of the filtrate vessel 52 as the filtrate enters along the tube 181. This nitrogen exhaust line is identified by the numeral 206 in FIG. 1, which communicates with the line 208 connected to a safety and maximum pressure valve 210.

Continuing with the description of the righthand portion of FIG. 1, a high pressure pump 212 is operated by compressed air entering along line 214 through a series of valves and solenoids, and is adapted to step up the pressure of nitrogen entering along the line 216 at 2,000 psi to a level of approximately 3,500 psi. The safety and maximum pressure valve 210 would typically be set at about 50 psi above the setting of the pump 212. These components, acting together, determine the effective nitrogen back pressure which the filtrate vessel 52 sees along the line 206. That back pressure normally does not fall below the pump setting of about 3,500 psi, and cannot rise above the setting of the safety and maximum pressure valve 210. This nitrogen back pressure similarly defines, along with the pressure exerted by the fluid compression vessel 35, the pressure differential across the porous cylindrical member 116. This pressure differential is preferably in the range from 0 to 500 psi.

It is appropriate now to summarize the filling and operation of the system disclosed above.

Essentially, the system is first filled and flushed with distilled water at atmospheric pressure. All air is purged from the system and distilled water also is present behind the porous cylindrical member, i.e. in the passages where filtrate will eventually move to the filtrate vessel 52.

At this stage, the piston 220 of the fluid compression vessel 35 is at the top, and high pressure exists below it in order to keep the fluid compression vessel empty. The filling vessel 20 is also empty.

Then, a certain quantity of test fluid is poured into the filling vessel from the hopper 22 and through the valve 24. Valve 24 is then closed and valve 19 is opened. Valve 39 is a backflushing valve and must be closed while the cleaning line valve 31 is open.

Next, the pressure in the compression vessel 35 is lowered (i.e. the pressure under the piston 220) so that approximately 400 ml of test fluid enters the compression vessel 35 along the line 30. As soon as the 400 ml has been taken into the compression vessel 35, the pressure of the latter is adjusted to be the same as the air supply of the valve 16.

At this point the distilled water is displaced from the fluid testing vessel 58 and the related systems by the test fluid from the fluid compression vessel 35 which is under about 100 psi. The flushing out of the distilled water continues until pure test fluid is seen to escape from the fluid testing vessel 58.

Then the positive displacement pump 134 is started. Next the pressure in the compression vessel 35 is increased to displace the 400 ml in the vessel through the system.

At this stage the filling vessel 20 is empty, as is the fluid compression vessel 35 (the piston 220 is at the top or its maximum travel). The fluid testing vessel 58 and the various passageways associated with it are filled with test fluid. All air and cleaning fluid has been displaced. The back (downstream side) of the porous cylindrical member 116 (the filter) is purged of air and filled with distilled water.

Returning to the filling vessel 20, the valve 19 is then closed and the valve 24 is opened. About 2.5 liters of premade filtrate are then poured into the filling vessel, whereupon the valve 24 is closed.

The pressure in the fluid compression vessel 35 is then lowered so that the 2.5 liters of premade filtrate will enter the compression vessel 35. As soon as all the fluid has emptied from the filling vessel 20, the pressure of the compression vessel 35 is adjusted to the same pressure as the air supply from the air pressure regulator 16. Then the valve 19 is closed.

At this point in time the filling vessel 20 is empty and the compression vessel 35 is full of premade filtrate. Test fluid is in the fluid testing vessel 58 and related portions, without any air being present.

The system is then ready for testing the fluid loss of a fluid.

The high pressure compressor which includes the pump 212 is then adjusted to the required pressure. The air pressure regulator 61 is then adjusted to the required pressure and the liquid pump 65 is started by energizing the solenoid valve 63.

At this point, the filtration collection line valve 45 should be closed and no filtration should be taking place. The nitrogen pressure will be increasing to the desired pressure, as well as the liquid pressure increasing to the desired pressure.

If it is desired to test the drilling mud under high temperatures simulating those found in the bore-hole, heat may now be applied to the fluid testing vessel 58. Referring briefly to FIG. 2, this is typically done by providing an aluminum collar 235 with internal heating means 237, surrounding the cylindrical member 80.

Returning to FIG. 1, the pump 134 can now be set to the desired flow rate, and when the temperature and pressure are at the desired levels the fluid testing vessel 58 can be pressurized. The filtrate collection line valve 45 is then opened to allow filtration to begin.

The filtration is allowed to continue for a preset time or until the filtrate volume has reached a particular quantity, or until premade filtrate needs to be replenished.

The foregoing will give a general overview of the basic steps involved in carrying out dynamic filtration with the apparatus set forth herein.

It will further be appreciated that the same steps can be taken, however, without turning on the positive displacement pump 134, thus resulting in a static fluid loss test for the drilling mud.

While one embodiment of this invention has been illustrated in the accompanying drawings and described hereinabove, it will be evident to those skilled in the art that changes and modifications may be made therein without departing from the essence of this invention as set forth in the appended claims.

I claim:

1. A bore hole hydraulics simulator for drilling fluid, comprising:
   a permeable partition in the shape of an open-ended sleeve enclosing a first volume,
   first means defining a second volume surrounding said sleeve, the second volume being adapted to receive filtrate passing across the permeable partition,
   second means for flowing the drilling fluid axially through said sleeve,
   third means for placing a pressure differential across the partition so as to promote the passage of filtrate into said second volume, and
   fourth means for collecting the filtrate entering the second volume.

2. The invention claimed in claim 1, in which a rod-like member is positioned centrally within said sleeve to simulate a drill-string.

3. The invention claimed in claim 2, which further includes means for heating the drilling fluid.

4. The invention claimed in claim 2, which further includes means for pressurizing both volumes above atmospheric pressure.

5. The invention claimed in claim 4, which further includes means for heating the drilling fluid.

6. The invention claimed in claim 2, in which the means for flowing the drilling fluid comprises a positive displacement pump.

7. The invention claimed in claim 2, which further includes means for heating the drilling fluid to a temperature in the range from 65° F. to 650° F., and means for pressurizing both volumes above atmospheric to a pressure up to about 3500 psi.

8. The invention claimed in claim 2, further including ultrasonic means within the rod-like member for measuring the thickness of the cake build-up on the permeable partition within the first volume.

9. The invention claimed in claim 8, in which the ultrasonic means includes an ultrasound generator means and an ultrasound receiving means, whereby an ultrasonic signal sent by the generator means can be reflected from a filter cake build-up and the echo received by the receiving means.

10. The invention claimed in claim 2, in which the fourth means for collecting the filtrate includes a vessel shaped such that a vertical measurement of the liquid level therewithin can be used to determine the volume of filtrate in the vessel, the vessel including ultrasonic means for measuring the heights of different liquid levels.

11. The invention claimed in claim 10, in which the vessel is an upright cylinder, and the ultrasonic means includes a generating means and a receiving means for ultrasound, located at the bottom of the vessel and in sound-conducting contact with liquid in the vessel.

12. The invention claimed in claim 11, in which said vessel further includes a further ultrasonic means by which to calibrate the first-mentioned ultrasonic means, said further ultrasonic means being adapted to project an ultrasound signal across a cavity of known dimension filled with filtrate, and to receive the echo therefrom, whereby the time taken for the ultrasound to traverse the cavity twice can be used to calibrate said first-mentioned ultrasonic means.

13. The invention claimed in claim 10, in which said ultrasonic means comprises an ultrasonic generator and receiver at the top of the vessel adapted to bounce an ultrasound signal off the surface of filtrate in the vessel, so that the time taken to send the signal and receive the echo for any given level can be known.

14. A method for testing filtration rate for a drilling fluid under dynamic conditions, comprising the steps:
   flowing the drilling fluid centrally along a permeable sleeve which divides a first volume within the sleeve and containing the drilling fluid from a second volume surrounding the sleeve and adapted to collect filtrate passing out through the permeable sleeve,
   placing a pressure differential across the sleeve so as to promote the passage of filtrate into said second volume, and collecting the filtrate passing into said second volume.

15. The method claimed in claim 14, including the further step of heating the drilling fluid.

16. The method claimed in claim 14, which further includes the step of pressurizing both volumes above atmospheric pressure.

17. The method claimed in claim 16, which further includes the step of heating the drilling fluid.

18. The method claimed in claim 14, in which the step of flowing the drilling fluid along the permeable sleeve is carried out by the use of a positive displacement pump.

19. The method claimed in claim 14, further including the step of positioning a rod-like member centrally within the sleeve to simulate a drill-string.

20. The method claimed in claim 19, which includes the further steps of heating the drilling fluid to a temperature in the range from 65° F. to 650° F., and pressurizing both volumes above atmospheric to a value up to about 3500 psi.

21. The method claimed in claim 19, including the further step of ultrasonically monitoring the thickness of the cake build-up on the permeable sleeve within the first volume, by using ultrasonic means mounted within the rod-like member.

22. The method claimed in claim 21, in which the step of monitoring the thickness of the cake build-up is carried out by sending an ultrasonic signal from an ultrasound generator within the rod-like member across to a built-up cake on the permeable sleeve, reflecting the same back from the built-up cake, and receiving the echo by an ultrasound receiving means, the ultrasound generator means and the ultrasound receiving means being part of the ultrasonic means.

23. The invention claimed in claim 14, in which the step of collecting the filtrate is carried out by providing a vessel shaped such that a vertical measurement of a liquid level therewithin can be used to determine the volume in the vessel, and passing filtrate from the second volume to the vessel.

24. The method claimed in claim 23, in which a height comparison for different liquid levels within the vessel is utilized to determine the filtration rate.

25. The method claimed in claim 24, in which the height comparison for the different liquid levels is carried out ultrasonically.

26. The method claimed in claim 25, in which the said vessel is an upright cylinder, and in which the step of comparing the heights of different liquid levels is carried out ultrasonically by an ultrasonic means including a generating means and a receiving means for ultrasound, the ultrasonic means being located at the bottom of the vessel and in sound-conducting contact with liquid in the vessel.

27. The method claimed in claim 26, further characterized by the step of calibrating the first-mentioned ultrasonic means by projecting an ultrasound signal across a cavity of known dimension filled with filtrate, receiving the echo therefrom, and recording the time taken for the ultrasound to traverse the cavity twice, whereby to calibrate said first-mentioned ultrasonic means.

28. The method claimed in claim 25, in which the ultrasonic height comparison of different liquid levels is carried out by generating an ultrasound signal from the top of the vessel, bouncing the same from the surface of the filtrate, and recording the time taken for the echo to return to the top.

29. A dynamic fluid loss testing system comprising:
means for flowing the drilling fluid axially through a permeable partition in the form of an open-ended sleeve, which divides a first volume surrounded by the sleeve and containing the drilling fluid from a second volume surrounding the sleeve and adapted to collect filtrate passing through the permeable partition,
means for placing a pressure differential across the partition so as to promote the passage of filtrate into said second volume,
means for collecting the filtrate passing into the second volume, and
means for continuously adding fluid to said first volume to compensate for the decrease resulting from the loss of filtrate passing into the second volume.

30. A bore hole hydraulics simulator system, comprising:
a closed loop circuit around which drilling fluid can pass, and means for forcing the drilling fluid to circulate in said circuit,
a permeable partition in the shape of an open-ended sleeve defining part of the circuit through which the drilling fluid circulates, the permeable partition dividing a volume within the sleeve containing the circulating drilling fluid from a further volume external to the sleeve adapted to collect filtrate passing through the permeable partition,
means for placing a pressure differential across the partition so as to promote the passage of filtrate therethrough,
means for collecting the filtrate passing through the porous partition, and
a fluid compression vessel filled with drilling fluid under pressure and communicating with the circuit around which the drilling fluid circulates, so that as filtrate is lost through said permeable partition, fluid can be added to the circuit around which the drilling fluid circulates, said closed loop circuit having a constant volume.

* * * * *